(12) United States Patent
Koulikov (10) Patent No.: US 10,634,608 B2
(45) Date of Patent: Apr. 28, 2020

(54) OPTICAL ABSORPTION SPECTROSCOPY BASED GAS ANALYZER SYSTEMS AND METHODS

(71) Applicant: Serguei Koulikov, Los Altos, CA (US)

(72) Inventor: Serguei Koulikov, Los Altos, CA (US)

( * ) Notice: Subject to any disclaimer, the term of this patent is extended or adjusted under 35 U.S.C. 154(b) by 0 days.

(21) Appl. No.: 16/416,200

(22) Filed: May 18, 2019

(65) Prior Publication Data

US 2019/0271641 A1    Sep. 5, 2019

Related U.S. Application Data

(63) Continuation of application No. 15/859,378, filed on Dec. 30, 2017, now Pat. No. 10,401,281.

(60) Provisional application No. 62/535,505, filed on Jul. 21, 2017.

(51) Int. Cl.
| | | |
|---|---|---|
| G01N 21/3504 | (2014.01) | |
| G01N 21/71 | (2006.01) | |
| G01N 33/15 | (2006.01) | |
| G01N 21/27 | (2006.01) | |
| G01N 21/31 | (2006.01) | |
| G01J 3/42 | (2006.01) | |
| G01N 21/39 | (2006.01) | |
| G01N 21/17 | (2006.01) | |

(52) U.S. Cl.
CPC ............ *G01N 21/3504* (2013.01); *G01J 3/42* (2013.01); *G01N 21/27* (2013.01); *G01N 21/31* (2013.01); *G01N 21/39* (2013.01); *G01N 21/716* (2013.01); *G01N 33/15* (2013.01); *G01N 2021/1704* (2013.01); *G01N 2021/1748* (2013.01); *G01N 2021/399* (2013.01); *G01N 2201/0612* (2013.01)

(58) Field of Classification Search
CPC .............. G01J 3/42; G01N 2021/1704; G01N 2021/1748; G01N 2021/399; G01N 21/27; G01N 21/31; G01N 21/3504; G01N 21/39; G01N 21/716; G01N 2201/0612; G01N 33/15
USPC ............................ 356/432–448, 243.2–243.8
See application file for complete search history.

(56) References Cited

U.S. PATENT DOCUMENTS 6,115,401 A * 9/2000 Scobey ............... H01S 3/08036
372/100

* cited by examiner

*Primary Examiner* — Tri T Ton (57) ABSTRACT

The present invention provides a system for measuring concentrations of trace gases in gas mixtures using an absorption spectroscopy method. The system comprising: a resonant optical cavity containing a gas mixture, a continuous-wave external cavity laser, a detector system for measuring an absorption of laser light by the gas in the resonant optical cavity, wherein the ratio of the round-trip length of the external cavity laser to the round-trip length of the resonant optical cavity or its inverse value is between N−0.2 and N+0.2, where N is a positive integer number.

20 Claims, 5 Drawing Sheets

OPTICAL ABSORPTION SPECTROSCOPY BASED GAS ANALYZER SYSTEMS AND METHODS

CROSS-REFERENCES TO RELATED APPLICATIONS

This application is a continuation application of U.S. Non-provisional application Ser. No. 15/859,378 filed Dec. 30, 2017, which claims the benefit of, and priority to, U.S. provisional Patent application No. 62/535,505 filed Jul. 21, 2017, the contents of both of which are hereby incorporated by reference.

BACKGROUND OF THE INVENTION

The present invention relates generally to trace gas detection and more specifically to cavity enhanced absorption spectroscopy systems and methods for measuring trace gases.

Traditionally, in standard applications of cavity enhanced absorption spectroscopy methods with resonant cavities, lasers with smooth frequency tuning behaviors are preferable. It is also important to have lasers with smooth frequency tuning behaviors for tunable diode laser absorption spectroscopy applications, e.g, TDLAS or Off Axis ICOS, where concentrations of absorbing gas species are measured by measuring absorption spectra of different species as function of wavelength and fitting them using spectral line-shape models. Unless a very precise wave-meter is used to measures the laser light frequency, any deviations in the laser tuning curves from ideal may cause errors in the reported concentration values.

In addition to that, if a DFB laser is used in a cavity enhanced laser based gas analyzer system as a light source, an electrical noise of the laser diode current causes an additional noise in the laser frequency. Moreover, any unwanted discontinuity in the laser current tuning, for example, due to the quantization noise of a finite resolution of a digital-to-analog converter, can be transferred to a discontinuity of the laser frequency.

Accordingly, there is a need for systems and methods for trace gas detection using lasers with improved performance coupled to resonance optical cavities.

SUMMARY OF THE INVENTION

The present invention provides systems and methods for measuring concentrations of trace gases in gas mixtures using absorption spectroscopy methods.

Embodiments of the present invention provide systems and devices for measuring concentrations of trace gases in analyzed gas mixtures with high accuracy using a resonance optical cavity, which contains a gas mixture to be analyzed, a laser coupled to the cavity, and a light sensitive detector. The optical cavity can include any type of cavity with two or more cavity mirrors, including a linear or a ring cavity. A laser that is capable of being frequency-scanned is coupled to the cavity through one of the cavity mirrors (i.e., the cavity coupling mirror). A detection method can be based on any of a variety of cavity enhanced optical spectroscopy (CEOS) methods, for example, cavity ring-down spectroscopy (CRDS) methods, or cavity enhanced absorption spectroscopy (CEAS) methods.

Embodiments of the present invention also provide a system comprising a laser source with a stepwise tuning curve where frequency steps are matched to the free spectral range (FSR) of a resonant cavity. An example of such laser source is an external cavity laser based on a DFB laser. At a specific range of the optical feedback created by the external cavity, the laser linewidth significantly decreases in comparison with a free running DFB laser and its spectral tuning curve becomes a stepwise function.

Positions of steps in the laser tuning curve can be tuned by adjusting the external cavity optical length. Such laser source can be fiber coupled to deliver the laser light to a resonant cavity by an optical fiber. Such laser source can also be optically isolated from external optical feedback sources. Laser light emitted by such laser source could also be amplified, modulated or interrupted by a SOA or a BOA. Laser light emitted by such laser source can also be modulated or interrupted by optical modulators, such as AOM, EOM, etc. When laser light emitted by such laser source is coupled to a resonant cavity, the coupling efficiency can be significantly increased because of two reasons: the laser line width narrows and the laser frequency tuning slope decreases on flattened parts of the stepwise tuning curve (the laser frequency becomes less sensitive to the laser current driver noise) compared to a free running DFB laser. This invention is both an apparatus and a method of using such laser source for the cavity enhanced optical absorption spectroscopy applications with resonant cavities.

DETAILED DESCRIPTION OF THE INVENTION

The present invention provides systems and methods for measuring concentrations of trace gases in gas mixtures using absorption spectroscopy methods. The optical absorption spectroscopy involves passing radiation through a sample, e.g., an analyte and measuring absorption property of the sample as a function of the radiation wavelength. For example, trace gas detection can be spectroscopically performed by taking measurements to detect the presence or absence of spectral absorption lines corresponding to the gas species of interest. Trace gas detection can be spectroscopically performed by taking measurements to quantify spectral absorption lines corresponding to the gas species of interest and to compute concentrations of analytes, gas pressure, and gas temperature. Spectroscopic analysis of isotopologues can also be performed.

One of the most important applications of the optical absorption spectroscopy technique is measuring gases in trace amounts. Concentrations of gases can be less than part-per-billion. The task becomes more challenging if relatively weak rotational-vibrational transitions in the NIR spectral range are measured for determining the trace gas concentration. Such measurements usually require high fineness resonant cavities, which effectively increase the path length of an interaction of laser light with trace gases. However, high fineness resonant optical cavities have rather narrow optical resonances, usually much more narrow than linewidth of lasers used for such applications, such as DFB lasers. This phenomenon drastically decreases in efficiency of the laser-to-cavity coupling. Making external cavity lasers based on DFB lasers as gain media helps to partially solve two problems: improving the laser-to-cavity coupling due to mere narrow linewidth of external cavity lasers and decreasing sensitivity of wavelength of the emitted light of such lasers to the electrical noise.

We use a term optical path length, or optical length, or optical distance meaning the product of the geometric length of the path light follows through the system, and the index of refraction of the medium through which it propagates.

According to an embodiment, a gas analyzer system for measuring a concentration of a component in a gas mixture, the system comprising: a resonant optical cavity containing said gas and having at least two cavity mirrors, one of which is a cavity coupling mirror containing a gas having a chemical species to be measured; a continuous-wave stepwise tunable external cavity laser emitting light optically coupled to the resonant optical cavity, an output of the laser is scanned across a range of frequencies including the frequency of said one of the plurality of cavity modes; mode matching optics configured to couple the laser light to the cavity via the cavity coupling mirror; a detector system for measuring an absorption of laser light by the gas in the resonant optical cavity, the detector system being operable to transmit a data signal corresponding the absorption of laser light by the gas in the resonant optical cavity; and a processor operable to conduct the absorption spectroscopy analysis of the gas sample based on the data signal. The roundtrip length of the cavity of the external cavity laser is close to the roundtrip length of the resonant optical cavity containing the measured gas mixture. When the optical feedback from the external cavity to the laser gain media is strong enough to produce a stepwise laser tuning curve, but weak enough to not skip some modes of the external laser cavity, the laser produces a stepwise tuning curve with a difference in frequencies of two adjusted steps closer to the free spectral range of the resonant cavity.

According to an embodiment, an external cavity laser comprises a means for adjusting an optical length of the external cavity of the laser to match a frequency of the lasing light to a frequency of one of the cavity modes of the resonant optical cavity. Such adjustment can be done by changing the physical length of the external cavity, for example by placing one of mirrors of the cavity on a translation stage or on a piezo transducer. Such adjustment can also be done by changing the optical length of one of the optical components of the external cavity, such as a phasor placed in the cavity, a lens, etc. The optical length of the optical path through a lens can be changed by changing the lens temperature, which affects the refractive index of the lens material. Such adjustment can also be done by changing the gas pressure inside the external cavity.

According to another embodiment, a resonant cavity comprises a means for adjusting an optical length of the resonant cavity to match the frequency of the lasing light to a frequency of one of the cavity modes of the resonant optical cavity. Such adjustment can be done by changing the physical length of the resonant cavity, for example by placing one of mirrors of the cavity on a piezo transducer. Such adjustment can also be done by changing the gas pressure inside the resonant cavity.

Figure 5:
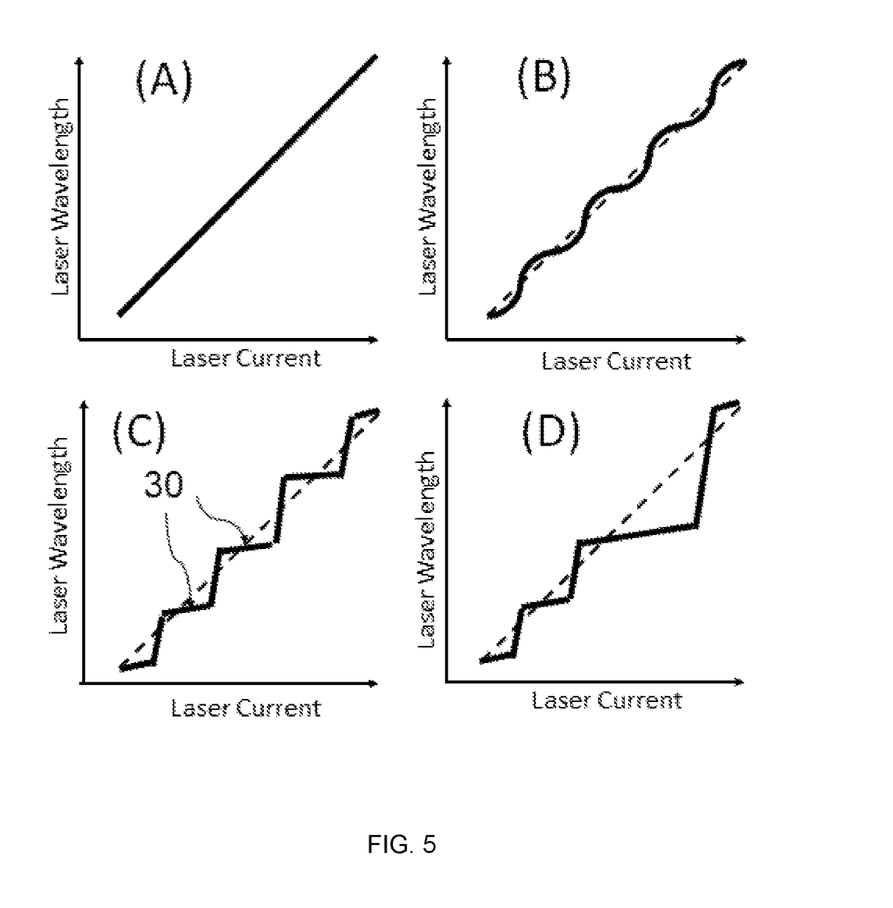
FIG. 5 illustrates four typical laser tuning curves of an external cavity laser, where a laser gain media is a DFB laser depending on intensity of the optical feedback sent to the gain media by the external cavity.

According to an embodiment, an external cavity laser comprises a means for adjusting an optical feedback intensity from one of mirrors forming the laser external cavity to a laser gain media to match steps of the laser tuning curve to the free spectral range of the resonant cavity. If the feedback is too weak, no steps are produced in the laser tuning curve. If the feedback is too strong, the steps can be wider than the free spectral range of the external cavity. With intermediate feedback intensity, the laser can be repeatedly tuned to any external cavity mode. The feedback intensity can be adjusted by placing any light intensity modulator inside the laser cavity. The feedback intensity can also be adjusted by tilting one of the mirrors of the external cavity or by misaligning another optical component in the laser cavity. FIG. 5 illustrates how the laser tuning curve may depend on the optical feedback to the gain media in an external laser cavity, wherein the media is a DFB laser. The feedback strength is increasing from FIG. 5A to FIG. 5D. FIG. 5A illustrates the laser tuning curve of a free running DFB laser with no feedback from any external to the DFB laser sources.

According to an embodiment, the external cavity laser comprises a single mode optical fiber as part of the external cavity of the laser. The optical feedback to the gain media can be produced by a reflection from one of the ends of the optical fiber. The optical feedback to the gain media can also be produced by a reflection from an optical component, which is a part of the external cavity. An example of such laser is a fiber coupled DFB laser without any optical isolator between a gain media and an optical fiber. If an optical collimator is used to collimate the laser beam emitted from the fiber, then a partial reflector can be placed at the collimated free space beam. When the partial reflector is perpendicular to the laser beam it reflects back to the fiber light emitted from the fiber. By tilting the partial reflector, the intensity of the optical feedback to the gain media can be adjusted. The phase of the stepwise tuning curve can be adjusted by changing the optical distance between the gain media and the partial reflector. The optical distance between the gain media and the partial reflector can be adjusted, for example, by changing a temperature of the optical fiber, by changing a mechanical stress in the fiber, or by a distance between the fiber and the partial reflector.

According to another embodiment, the external cavity laser is optically isolated from the resonant cavity. It can be done by placing an optical isolator in the optical path between the laser and the cavity. A Faraday isolator is an example of such optical isolator.

According to an embodiment, the gas analyzer system for measuring a concentration of a component in a gas mixture comprising an optical amplifier in an optical path between the continuous-wave stepwise tunable external cavity laser and the resonant cavity. The optical amplifier selected from the group consisting of a Booster Optical Amplifier (BOA) and a Semiconductor Optical Amplifier (SOA), the optical amplifier is capable to amplify or/and to interrupt laser light emitted by the laser. The amplifier can be a free space amplifier or a fiber coupled amplifier. The laser can be optically isolated from the amplifier. The amplifier can also be optically isolated from the resonant cavity. The amplifier can be used to amplify the laser light intensity. The amplifier can also be used to interrupt the laser light. For example, the amplifier can be used to interrupt the laser light if the gas analyzer is based on the CRDS technique.

According to an embodiment the gas analyzer system for measuring a concentration of a component in a gas mixture comprising an optical modulator in an optical path between the continuous-wave stepwise tunable external cavity laser and the resonant cavity, wherein optical modulator selected from the group consisting of an Electro-Optic Modulator (EOM) and an Acousto-Optic Modulator (AOM), the optical modulator is capable to modulate the laser light intensity emitted by the laser. The laser can be optically isolated from the modulator. The modulator can also be optically isolated from the resonant cavity. The modulator can be used to interrupt the laser light. For example, the modulator can be used to interrupt the laser light if the gas analyzer is based on the CRDS technique.

According to another embodiment the detector system includes a photo-detector configured to measure an intensity of intra-cavity light. The photo-detector can be a photo-diode, a photoresistor, photovoltaic detector, or another type of photo-detector.

According to an embodiment, the optical length between the photo-detector and the cavity mirror used to transmit the light measured by the photo-detector is close to half of the roundtrip optical length of the resonant cavity. This arrangement permits to minimize an effect of spectral ripples created by the light scattered or reflected from the detector and coupled back to the resonant cavity.

According to another embodiment the optical length of the optical path between one of the sources of unwanted scattered or reflected light coupled to the resonant cavity and the coupling mirror of the resonant cavity is close to half of the roundtrip optical length of the resonant cavity. Usually all optical components scatter light. Sources of the light scattering can be defects in optical coatings, roughness of surfaces of optical components, or bulk defects in optical components. These defects created so called coupled cavities with the resonant cavity. By placing an optical component with strong scattering or reflections coupled back to the cavity at the specify distance one can minimize an effect of spectral ripples created by this optical component.

According to another embodiment, an optical absorption spectroscopy based gas analyzer system for measuring a concentration of a component in a gas mixture, the system comprising: an optical cell containing a gas having a chemical species to be measured; a continuous-wave stepwise tunable external cavity laser emitting light entering the cell, the external cavity laser having a semiconductor distributed feedback laser (DFB) as gain media, wherein an output of the DFB laser is scanned across a range of the plurality of cavity modes of the external cavity; a detector system for measuring the intensity of the laser beam after the laser beam passes through the gas in the optical cell, the detector system being operable to transmit a data signal corresponding to the intensity of the laser beam after the laser beam passes through the gas in the optical cell; and a processor operable to conduct the absorption spectroscopy analysis of the gas sample based on the data signal; wherein steps in a laser tuning curve are used as frequency markers in an analysis of measured spectra.

According to yet another embodiment, the cavity of the external cavity laser can be temperature controlled.

According to an embodiment the optical cell is a multi-pass spectroscopic absorption optical cell.

Figure 1:
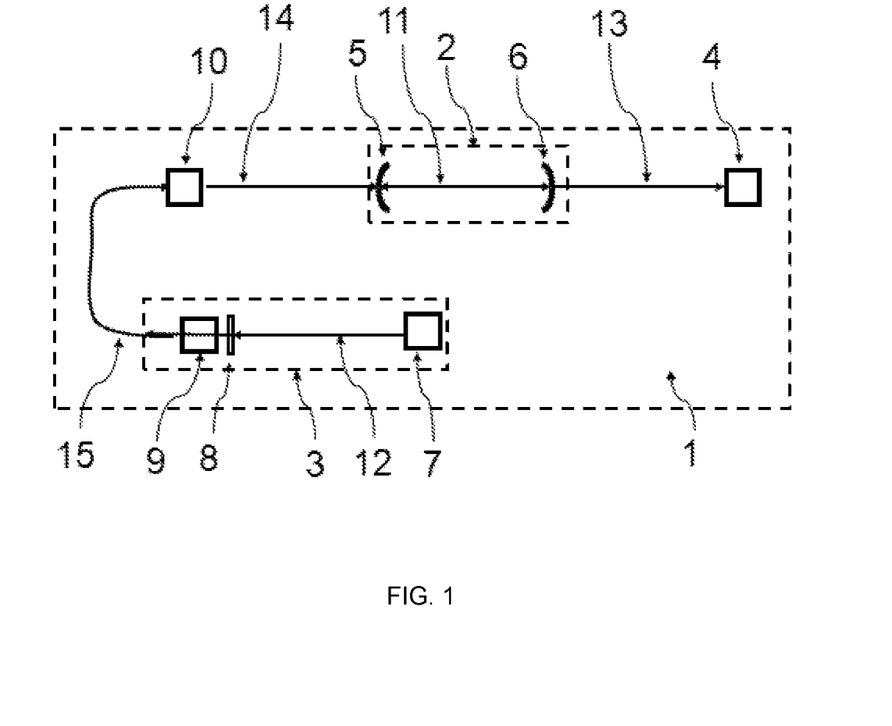
FIG. 1 illustrates a cavity enhanced absorption spectroscopy system according to one embodiment.

FIG. 1 is a schematic diagram of a system 1 of the present invention. In FIG. 1, light beams are illustrated by solid lines. For clarity of presentation, various standard elements such as lenses and mirrors used for focusing and directing beams are not described; such elements are well known in the art. Processor and electrical connections are not shown. System 1 comprises resonant optical cavity 2 of optical cavity length 11 containing a gas and having at least two cavity mirrors, one of which is cavity coupling mirror 5, another mirror 6 is used to transmit the light measured by the photo-detector. System 1 also comprises continuous-wave stepwise tunable external cavity laser 3 of optical cavity length 12 emitting light optically coupled to the resonant optical cavity 2, wherein the external cavity laser comprises semiconductor distributed feedback laser 7 as gain media and output coupler 8 forming a laser cavity; mode matching optics 10 configured to couple the laser light to resonant cavity 2 via cavity coupling mirror 5. System 1 also comprises a detector system 4 for measuring the absorption of laser light by the gas in resonant optical cavity 2, detector system 4 being operable to transmit a data signal corresponding the absorption of laser light by the gas in resonant optical cavity 2, detector system 4 separated from mirror 6 by optical length 13. Continuous-wave stepwise tunable external cavity laser 3 is optically isolated from cavity 2 by optical isolator 9. Continuous-wave stepwise tunable external cavity laser 3 is fiber coupled to optical fiber 15. Mode matching optics 10, which can be a source of scattered light coupled back to cavity 2 is separated from coupling mirror 5 by optical length 14.

Figure 2:
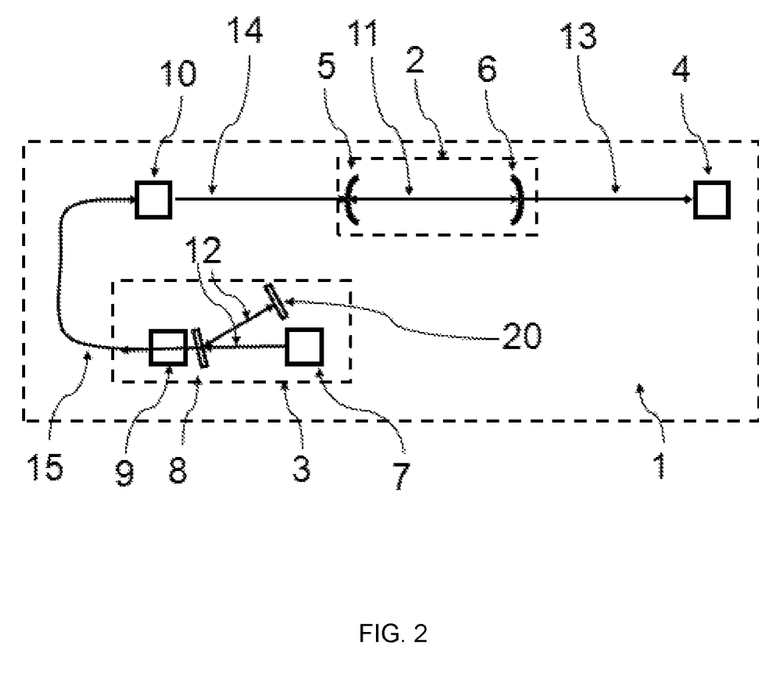
FIG. 2 illustrates a cavity enhanced absorption spectroscopy system according to another embodiment.

FIG. 2 is another schematic diagram of system 1 of the present invention. In FIG. 2, light beams are illustrated by solid lines. For clarity of presentation, various standard elements such as lenses and mirrors used for focusing and directing beams are not described; such elements are well known in the art. Processor and electrical connections are not shown. System 1 comprises resonant optical cavity 2 of optical cavity length 11 containing a gas and having at least two cavity mirrors, one of which is cavity coupling mirror 5, another mirror 6 is used to transmit the light measured by the photo-detector. System 1 also comprises continuous-wave stepwise tunable external cavity laser 3 of optical cavity length 12 emitting light optically coupled to the resonant optical cavity 2, wherein the external cavity laser comprise a semiconductor distributed feedback laser 7 as gain media, output coupler 8, and another mirror 20 forming a laser cavity; mode matching optics 10 configured to couple the laser light to resonant cavity 2 via cavity coupling mirror 5. System 1 also comprises detector system 4 for measuring absorption of laser light by the gas in resonant optical cavity 2, detector system 4 being operable to transmit a data signal corresponding the absorption of laser light by the gas in resonant optical cavity 2, detector system 4 separated from mirror 6 by optical length 13. Continuous-wave stepwise tunable external cavity laser 3 is optically isolated from cavity 2 by optical isolator 9. Continuous-wave stepwise tunable external cavity laser 3 is fiber coupled to optical fiber 15. Mode matching optics 10, which can be a source of scattered light couple back to cavity 2 is separated from coupling mirror 5 by optical length 14.

Figure 3:
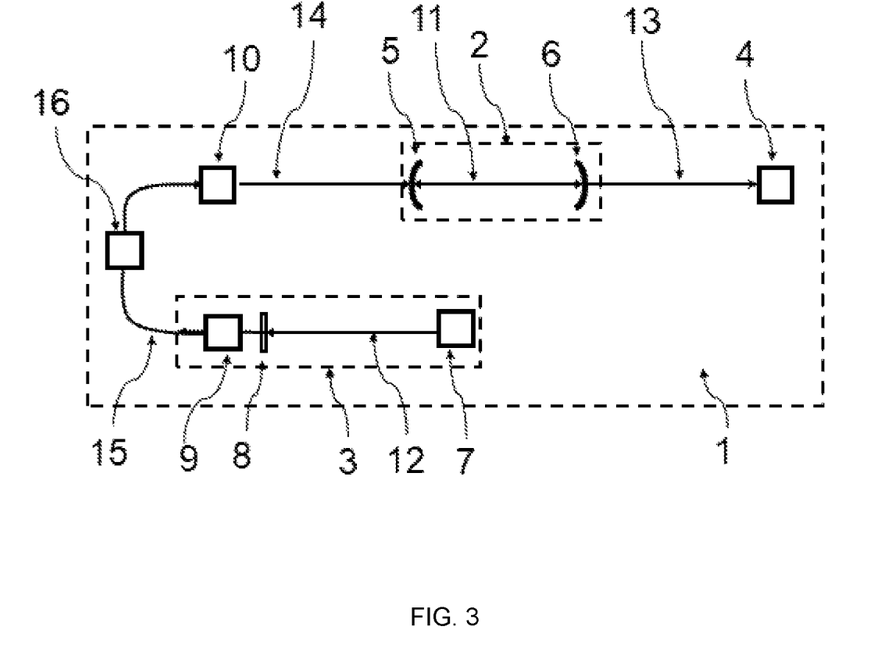
FIG. 3 illustrates a cavity enhanced absorption spectroscopy system according to yet another embodiment.

FIG. 3 is another schematic diagram of a system 1 of the present invention. In FIG. 3, light beams are illustrated by solid lines. For clarity of presentation, various standard elements such as lenses and mirrors used for focusing and directing beams are not described; such elements are well known in the art. Processor and electrical connections are not shown. System 1 comprises resonant optical cavity 2 of optical cavity length 11 containing a gas and having at least two cavity mirrors, one of which is cavity coupling mirror 5, another mirror 6 is used to transmit the light measured by the photo-detector. System 1 also comprises continuous-wave stepwise tunable external cavity laser 3 of optical cavity length 12 emitting light optically coupled to the resonant optical cavity 2, wherein the external cavity laser comprise sa semiconductor distributed feedback laser 7 as gain media and output coupler forming a laser cavity; mode matching optics 10 configured to couple the laser light to resonant cavity 2 via cavity coupling mirror 5. System 1 also comprises detector system 4 for measuring absorption of laser light by the gas in resonant optical cavity 2, detector system 4 being operable to transmit a data signal corresponding the absorption of laser light by the gas in resonant optical cavity 2, detector system 4 separated from mirror 6 by optical length 13. Continuous-wave stepwise tunable external cavity laser 3 is optically isolated from cavity 2 by optical isolator 9. Continuous-wave stepwise tunable external cavity laser 3 is fiber coupled to optical fiber 15. Mode matching optics 10, which can be a source of scattered light couple back to cavity 2 is separated from coupling mirror 5 by optical length 14. The fiber coupled optical amplifier or optical modulator 16 is placed between continuous-wave stepwise tunable external cavity laser 3 and resonant optical cavity 2.

Figure 4:
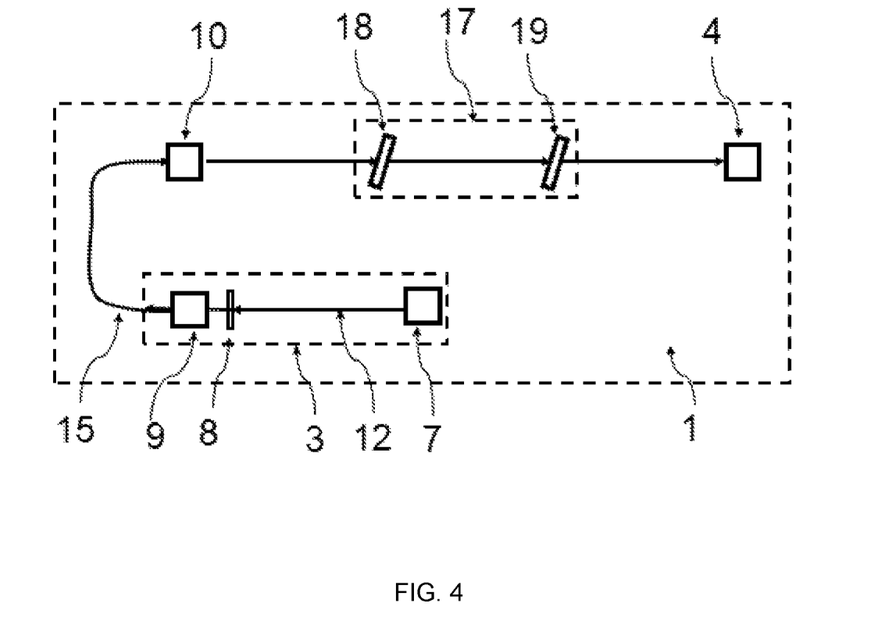
FIG. 4 illustrates an optical absorption spectroscopy system using a gas cell according to another embodiment.

FIG. 4 is a schematic diagram of a system 1 of the present invention. In FIG. 4, light beams are illustrated by solid lines. For clarity of presentation, various standard elements such as lenses and mirrors used for focusing and directing beams are not described; such elements are well known in the art. Processor and electrical connections are not shown. System 1 comprises optical cell 17 containing a gas and having at least two cell windows, one of which is cell coupling mirror 18, another window 19 is used to transmit the light measured by the photo-detector. System 1 also comprises continuous-wave stepwise tunable external cavity laser 3 emitting light optically coupled to optical cell 17, wherein the external cavity laser comprise semiconductor distributed feedback laser 7 as gain media and output coupler 8 forming a laser cavity; mode matching optics 10 configured to transmit the laser light to optical cell 17 via cell window 18. System 1 also comprises system 4 for measuring the intensity of the laser beam after the laser beam passes through the gas in the optical cell 12, detector system 4 being operable to transmit a data signal corresponding the absorption of laser light by the gas in optical cell 17. Continuous-wave stepwise tunable external cavity laser 3 is optically isolated from optical cell 17 by optical isolator 9. Continuous-wave stepwise tunable external cavity laser 3 is fiber coupled to optical fiber 15. Mode matching optics 10 is used to form a laser beam entering optical cell 17.

FIG. 5 illustrates how a laser tuning curve may depend on the optical feedback to the gain media in an external laser cavity, wherein the media is a DFB laser. The feedback strength is increasing from FIG. 5A to FIG. 5D. FIG. 5A illustrates the laser tuning curve of a free running DFB laser with no feedback from any external to the DFB laser sources. FIG. 5B illustrates an effect of a weak feedback when smooth waves are appeared on the tuning curve. FIG. 5C shows an effect of an intermediate feedback when sharp transitions are appeared on the tuning curve. In the intermediate feedback regime steps are almost equidistant in the frequency space and correspond to the external cavity free spectral range. FIG. 5D shows an effect of a strong feedback when steps on the tuning curve become irregular and differences of frequencies of two adjusted steps exceed the external cavity free spectral range. The laser tuning curve of a DFB laser with no feedback from any external to the DFB laser sources are shown in FIG. 5B, FIG. 5C, and FIG. 5D by dash lines. Due to the optical feedback steps 30 are formed how the laser tuning curve.

The invention claimed is:

1. A gas analyzer system for measuring a concentration of a component in a gas mixture, the system comprising: a resonant optical cavity containing said gas and having at least two cavity mirrors, one of which is a cavity coupling mirror; a continuous-wave external cavity laser emitting light optically coupled to the resonant optical cavity, wherein the external cavity laser comprises a semiconductor gain medium, an output coupler, a first tunable narrow band spectral filter spatially separated from the gain medium and capable of filtering a single longitudinal mode in the laser cavity across a bandwidth of the gain medium; mode matching optics configured to couple the laser light to the resonant optical cavity via the cavity coupling mirror; a detector system for measuring an absorption of the laser light by the gas in the resonant optical cavity, wherein the detector system being operable to transmit a data signal corresponding to the absorption of laser light by the gas in the resonant optical cavity; and a processor operable to conduct the absorption spectroscopy analysis of the gas sample based on the data signal, wherein the ratio of the round-trip optical cavity length of the external cavity laser to the round-trip optical cavity length of the resonant optical cavity or its inverse value is between N−0.2 and N+0.2, where N is a positive integer number.

2. The system of claim 1, wherein the external cavity laser further comprising an actuator communicatively coupled to a component of the external cavity laser and capable to change a position of the component for adjusting an optical length of the cavity of the external cavity laser, wherein an optical path of an intra-cavity laser beam depends on the position of the component.

3. The system of claim 1, wherein the first tunable narrow band spectral filter selected from the group consisting of a dispersive prism, a diffraction grating, a solid etalon filter, a Fabry-Pérot etalon, a resonant optical cavity, and an optical Vernier filter.

4. The system of claim 1, wherein the external cavity laser is an optical feedback sensitive laser coupled by optical feedback to the resonant optical cavity.

5. The system of claim 1, further comprising a wavemeter for measuring a wavelength of the laser light.

6. The system of claim 1, wherein the external cavity laser further comprising a second tunable narrow band spectral filter for narrowing a spectral line-width of the laser light.

7. The system of claim 1, wherein the external cavity laser further comprising a polarization filter capable of selecting a polarization state of the laser light.

8. The system of claim 1, further comprising a single mode optical fiber in an optical path between the external cavity laser and the resonant optical cavity.

9. The system of claim 1, further comprising a means for adjusting an optical length of the resonant optical cavity.

10. The system of claim 1, further comprising an optical isolator in an optical path between the external cavity laser and the resonant optical cavity for isolating the external cavity laser from the resonant optical cavity.

11. The system of claim 1, further comprising an optical amplifier in an optical path between the external cavity laser and the resonant optical cavity, wherein the optical amplifier selected from the group consisting of a Booster Optical Amplifier and a Semiconductor Optical Amplifier, and the optical amplifier is capable of amplifying the laser light emitted by the laser.

12. The system of claim 1, further comprising an optical modulator in an optical path between the external cavity laser and the resonant cavity, wherein the optical modulator selected from the group consisting of a Booster Optical Amplifier, a Semiconductor Optical Amplifier, an Electro-Optic Modulator, and an Acousto-Optic Modulator, and the optical modulator is capable of modulating the laser light emitted by the laser.

13. The system of claim 1, wherein the detector system includes a photo-detector configured to measure an intensity of the light transmitted through the resonant optical cavity.

14. The system of claim 13, wherein an optical length between the photodetector and the cavity mirror used to transmit the light measured by the photodetector is close to half the roundtrip optical length of the resonant optical cavity.

15. The system of claim 1, further comprising an optical isolator in an optical path between the resonant optical cavity and the detector system for isolating the resonant optical cavity from any light scattered or reflected from the detector system.

16. The system of claim 1, wherein an optical length of optical path between one of the sources of unwanted scattered or reflected light coupled to the resonant optical cavity and one of mirrors of the resonant optical cavity is close to half of the roundtrip optical length of the resonant optical cavity.

17. The system of claim 1, further comprising a temperature sensor for measuring the temperature of the resonant optical cavity, a pressure sensor for measuring the pressure of the gas in the resonant optical cavity, a temperature control element configured to control the temperature of the gas in the resonant optical cavity, and a pressure control element configured to control the pressure of the gas in the resonant optical cavity.

18. The system of claim 1, further comprising a means for controlling a gas flow through the resonant optical cavity.

19. The system of claim 1, wherein the resonant optical cavity is disposed in a housing enclosure that provides an airtight seal for the resonant optical cavity, and wherein the temperature and the pressure of a gas in the housing enclosure are actively controlled.

20. The system of claim 1, further comprising a temperature sensor for measuring the temperature of the external cavity laser, and a temperature control element configured to control the temperature of the external cavity laser.

* * * * *